United States Patent [19]

Sayka et al.

[11] Patent Number: 5,392,113
[45] Date of Patent: Feb. 21, 1995

[54] SEMICONDUCTOR WAFER DEFECT MONITORING

[75] Inventors: Anthony Sayka; Stacy W. Hall, both of San Antonio; Judy U. Galloway, Fairoaks; Pierre Leroux; Bryan D. Schmidt, both of San Antonio; Daniel D. Siems, Boerne; Henry B. Taylor, III, San Antonio; Edward R. Vokoun, Boerne, all of Tex.

[73] Assignee: VLSI Technology, Inc., San Jose, Calif.

[21] Appl. No.: 954,200

[22] Filed: Sep. 30, 1992

[51] Int. Cl.⁶ .................................. G01N 21/88
[52] U.S. Cl. ............................. 356/237; 250/572
[58] Field of Search .............. 356/237, 239, 371, 445, 356/429–431, 338, 241; 250/562, 563, 571, 572; 358/106; 359/798, 802, 882, 368

[56] References Cited

U.S. PATENT DOCUMENTS

| | | | |
|---|---|---|---|
| 3,891,320 | 6/1975 | Kimura et al. | 356/371 |
| 4,284,356 | 8/1981 | Heilman | 356/430 |
| 4,342,515 | 8/1982 | Akiba et al. | 356/237 |
| 4,601,576 | 7/1986 | Galbraith | 356/237 |
| 4,672,437 | 6/1987 | Casper | 356/241 |
| 4,718,760 | 1/1988 | Chikama | 356/237 |
| 4,779,988 | 10/1988 | Horiguichi | 356/445 |
| 5,017,798 | 5/1991 | Murakami et al. | 356/431 |
| 5,162,807 | 11/1992 | Kohno | 356/237 |
| 5,208,648 | 5/1993 | Batchelder et al. | 356/239 |
| 5,289,267 | 2/1994 | Busch et al. | 356/394 |

FOREIGN PATENT DOCUMENTS 45208  10/1977  Japan ................. 359/368

*Primary Examiner*—Hoa Q. Pham
*Attorney, Agent, or Firm*—Hickman & Beyer

[57] ABSTRACT

Method and apparatus for detecting the presence of selected types of defects, such as chemical stains from a liquid photoresist material or a liquid dielectric material, on a non-visible chosen surface of a semiconductor water that has undergone at least one processing step. In one embodiment, a support substrate for, the wafer is provided that has a highly reflecting surface adjacent to the chosen surface. The reflecting surface and the chosen surface are moved apart, and the chosen surface is illuminated with light to form an optical image of the chosen surface. The optical image of the chosen surface is reflected in the reflecting surface, and the reflected optical image is examined for the presence of selected types of defects. In another embodiment, a portion of this reflecting surface is initially contiguous to the chosen surface. A selected defect, if any, on the chosen surface changes a surface characteristic of the reflecting surface so that the presence of this defect on the chosen surface is visually perceptible on the reflecting surface.

21 Claims, 2 Drawing Sheets

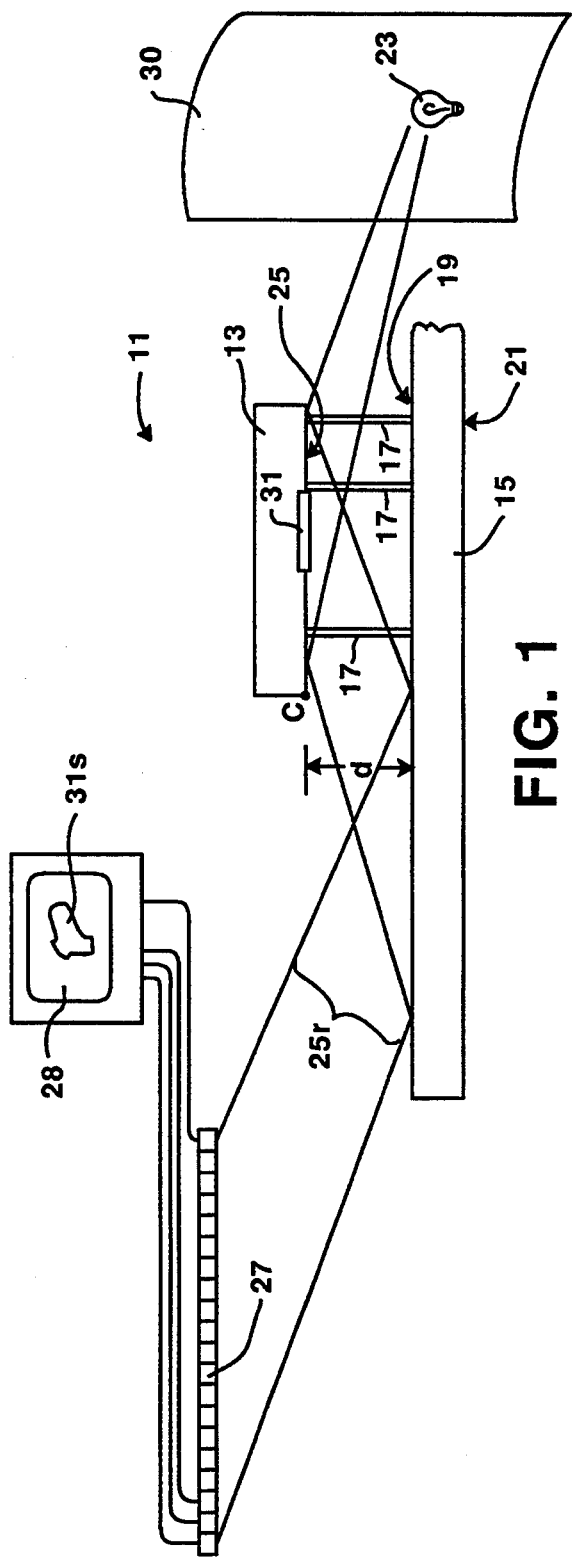
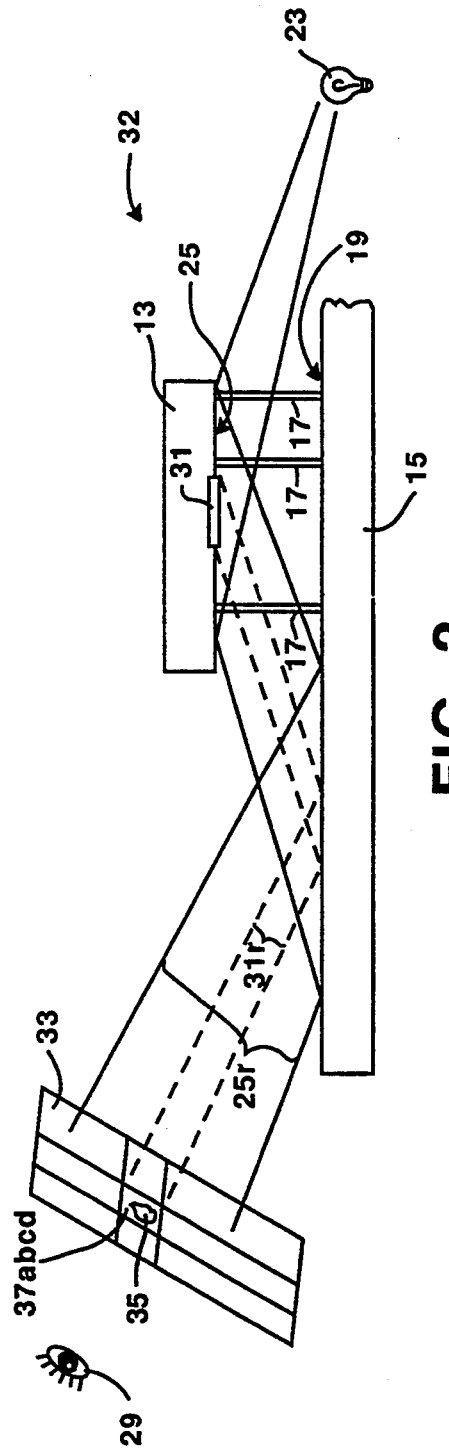

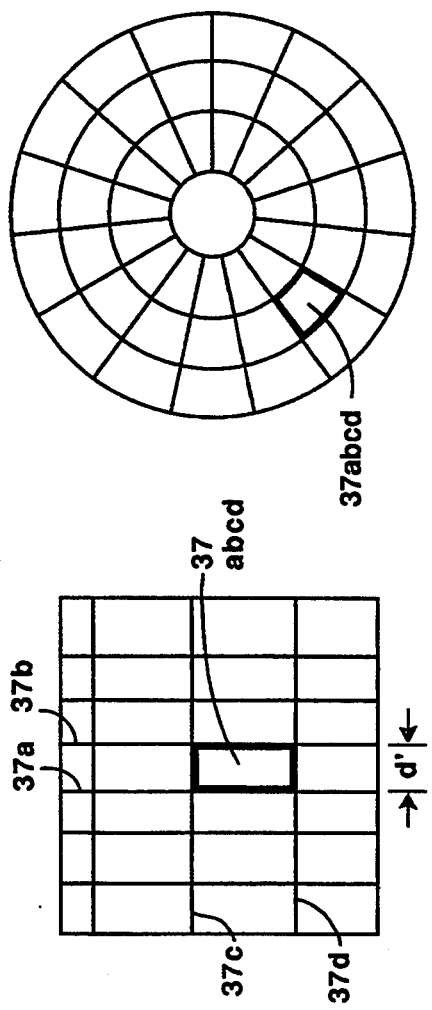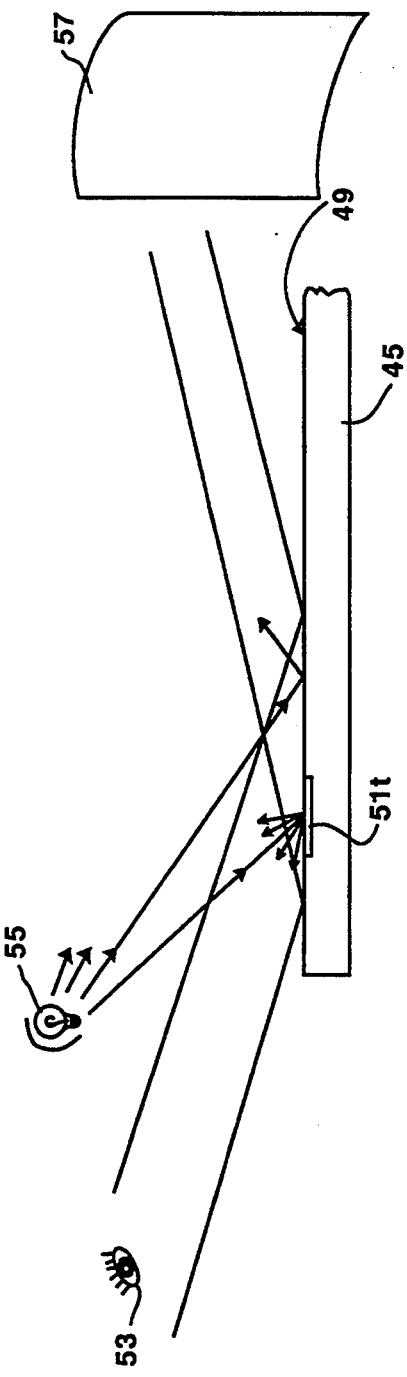

SEMICONDUCTOR WAFER DEFECT MONITORING

BACKGROUND OF THE INVENTION

1. Field of the Invention

This invention relates to detection of the presence or absence of defects, such as photoresist or electron beam resist stains, on a non-visible surface of a semiconductor wafer during wafer processing.

2. Background of the Technical Art

When a semiconductor wafer is processed to produce one or more integrated circuits (ICs), a semiconductor substrate, such as a silicon wafer, is provided. The integrated circuit is then constructed on the semiconductor substrate. Certain parts of the IC may require a selective process, such as chemical vapor deposition, chemical etching or ion implantation as part of the wafer processing. In these selective processes, photoresist ($\Phi$R) material or electron beam resist (EBR) material is laid down (and later removed) to selectively expose certain parts of a substrate or wafer face for the particular processing step. The processing step may be chemical vapor deposition, chemical etching, ion implantation or a similar processing step. The exposed or "front" wafer surface is observed directly after application of the $\Phi$R or EBR material to that surface. However, a non-visible or "back" surface of the wafer rests upon or is adjacent to a support surface and normally cannot be observed. An unwanted portion of the $\Phi$R or EBR material used on a wafer front face occasionally appears on the wafer back surface. This unwanted material can produce chemical stains that degrade either the performance or the appearance of the wafer or of an IC fabricated on the wafer, or that interfere with proper operation of subsequently applied equipment.

During certain semiconductor wafer processing steps, a support surface such as a chillplate, maintained at a temperature that is less than the wafer temperature, is placed contiguous to a back surface of the wafer to reduce the temperature of the wafer. When this temperature reduction occurs, certain unwanted semiconductor processing materials that are present on the back surface of the wafer may change phase and produce a chemical stain or other defect on the back surface and/or on the chillplate surface that is contiguous to the back surface.

What is needed is an technique that allows such stains or similar defects on a back surface of a semiconductor wafer to be detected as soon as possible after such stains or defects first appear in the processing of a wafer. Preferably, this technique would allow the location and physical extent of the defect(s) to be determined visually and would allow the severity of the defect(s) to be evaluated without manually removing the wafer from its support surface or chillplate surface.

SUMMARY OF THE INVENTION

These needs are met by the invention, which provides methods and apparatus for detecting the presence of such defects. At least one processing step is performed on a semiconductor wafer. An optical image of the back surface of the wafer is formed, and the optical image of the wafer back surface is examined to determine if the selected defect is present on that surface. The back surface of the wafer is usually hidden from view so that formation of an optical image of the chosen surface requires additional steps. The disclosed embodiments of the invention provide several alternatives or approaches for forming an optical image of the back surface without requiring that the wafer be rotated or moved manually in order to directly view the back surface.

In one approach, the wafer is displaced some distance from a support surface or chillplate surface (hereafter referred to as a "support surface" for convenience) for the wafer, where the support surface has initially been given a reflective coating. An optical image of the support surface is formed by reflection from the reflective surface, and this image is examined. In another approach, an image of the defect, if any, on the wafer chosen surface is initially transferred to the contiguous support substrate surface. The support substrate is translated away from the wafer, and this support substrate surface is examined to determine whether a defect is present on the chosen surface. In the embodiments, the only mechanical action required, if any, on the wafer is a simple translation of the chosen surface. The examination procedure is straightforward and may be performed with a small increase in the time required for semiconductor processing. Additional features and advantages of the invention are illustrated by the preferred embodiments set forth below.

BRIEF DESCRIPTION OF THE DRAWINGS

FIG. 1 is an elevation view of a first embodiment of the invention, where a wafer is displaced from a support surface by a known distance.

FIG. 2 is an elevation view of a second embodiment, used to identify the position(s) of the defects on a wafer back face.

FIGS. 3A and 3B illustrate two suitable quadrilateral patterns that can be used on a wafer back face with the mode of the second embodiment illustrated in FIG. 2.

FIGS. 4 and 5 are elevation views of a third embodiment of the invention, where a wafer is initially contiguous to and subsequently spaced apart from its support surface.

DETAILED DESCRIPTION OF THE PREFERRED EMBODIMENTS

Reference is now be made in detail to the preferred embodiments of the invention, examples of which are illustrated in the accompanying drawings. Although the invention will be described in conjunction with the preferred embodiments, it should be understood that these illustrations are not intended to limit the invention to those embodiments. The invention is intended to cover alternatives, modifications and equivalents, which may be included within the spirit and scope of the invention, as defined by the appended claims.

FIG. 1 illustrates a first embodiment 11 of the invention, in which a wafer 13 that is being processed is displaced from a support substrate 15, such as a chillplate, by a selected distance d by three or more support pins 17. The support pins 17 project through, and may be withdrawn into, the support substrate 15. The support substrate 15 is preferably made of a material such as quartz. A light wavelength $\lambda 0$ is chosen so that a stain or similar defect on the back face of the wafer 15 produces an image which, when illuminated by this light, differs substantially from the image that would be produced by a wafer back surface that is free of such defects. The wavelength $\lambda 0$ may also be chosen so that the support substrate material is relatively transparent to light at that wavelength. The support substrate 15 has a front surface 19 (or, attentively, a back surface 21) that is highly reflective for light at a selected wavelength $\lambda 0$. The support substrate 15 is adjacent to a chosen surface 25 of the wafer that is to be examined for the presence of a class of defects including EBR and/or $\Phi$R chemical stains. EBRs and $\Phi$Rs as well as certain dielectrics may be applied to a second surface of wafer 13 to form a desirable coating. They may be applied as a liquid by a spin-on coating technique, for example. In such techniques, portions of this liquid sometimes appear on the chosen surface. The chillplate may be a metal coated with teflon with a cooling liquid circulating in the metal.

A light source 23, preferably of small physical extent relative to the size of the chosen or back surface, produces light that contains the selected wavelength $\lambda 0$. The light source 23 is positioned below the wafer 13 at a selected set of coordinates ($\Delta x$, $\Delta y$, $\Delta z$) relative to a center C of the wafer chosen surface 25. The light source 23 illuminates the wafer chosen surface 25, forms an optical image of the chosen surface, and is reflected at the highly reflective surface 19 (or 21) of the substrate 15. A reflected image 25r of the chosen surface 25 of the wafer 13 is received by a CCD array or other suitable optical sensor array 27, or is viewed by the eye 29 of an observer. If a stain or similar defect 31 (shown in exaggerated thickness in FIG. 1) is present on the wafer chosen surface 25, this defect will manifest itself as a discoloration of this portion 31r (FIG. 2) of the reflected image. This discolored portion 31r will differ from the remainder of the reflected image of the wafer chosen surface that is free of such defects. The optical sensor array 27 may be used to form and display a defect image 31s on a screen 28 of any defect sensed by the sensor array on the chosen surface 25.

In the simplest mode of operation of this first embodiment, an observer's eye 29 or a CCD array 27 scans the reflected image 25r visually. The eye 29 or CCD array 27 thereby determines whether any portion of this reflected image is discolored or manifests any other visually perceptible difference relative to the remainder of the reflected image. If some portion of the reflected image 25r manifests a visually perceptible difference from the remainder of the reflected image, the wafer chosen surface 25 is determined to have a $\Phi$R or EBR stain or a similar defect thereon. Otherwise, the wafer chosen surface 25 is determined to have no defect from this class of possible defects.

In a second embodiment 32 of the invention, illustrated in FIG. 2, a transparent substrate 33 having a grid of lines thereon is provided in a plane or suitable curved surface that is approximately perpendicular to the direction of travel of the reflected image 25r of the wafer chosen surface 25. Grid lines 37a, 37b, 37c, 37d, etc. are arranged on the transparent substrate 33 to correspond to imaginary lines drawn at uniform intervals on the wafer chosen surface 25. Two consecutive grid lines 37a and 37b, oriented in a first direction, and two consecutive grid lines 37c and 37d, oriented in a second perpendicular direction, define a quadrilateral 37abcd of the grid on the transparent substrate 33. Each such quadrilateral 37abcd corresponds to a quadrilateral (not explicitly shown) on the wafer chosen surface 25. The observer's eye 29, fixed at a selected position and orientation, visually scans the portion of the reflected image 25r that is limited by the grid lines such as 37a, 37b, 37c, 37d, etc. on the transparent substrate 33. This visual scan detects any visually perceptible defects on the quadrilateral 37abcd. A visually perceptible defect 35 that appears in the quadrilateral 37abcd on the transparent substrate 33 is assigned to a corresponding quadrilateral, on the wafer chosen surface 25.

Let S be the collection of all quadrilaterals 39abcd on the wafer chosen surface 25 that correspond to a quadrilateral 37abcd on the transparent substrate 33 in which a visually perceptible difference appears. S is the set of all quadrilaterals on the wafer chosen surface 25 where a defect 31 appears. In this third mode of the first embodiment, the location(s) of the defect(s) 31 on the wafer chosen surface 25 can be identified. A defect 31 may extend over one or more quadrilaterals 39abcd on the wafer chosen surface 25. This identification would be useful if the wafer chosen surface 25 is to be reworked, or if IC chips corresponding to non-defect areas of the wafer 13 are to be salvaged.

Consecutive grid lines, such as 37a and 37b, of a quadrilateral 37abcd may be spaced apart a distance d' as small as one or a few mm, corresponding to a separation distance $d'' \approx 1$ mm of consecutive grid lines on the wafer chosen surface 25. FIG. 2 illustrates a suitable grid line pattern that corresponds to a rectangular quadrilateral pattern, shown in FIG. 3A, on the wafer chosen surface 25. However, the quadrilateral pattern on the wafer chosen surface 25 may have other shapes as well, such as a plurality of circular section quadrilaterals shown in FIG. 3B.

FIG. 4 illustrates a third embodiment 41 of the invention, wherein a wafer 43 is contiguous to and supported by a support substrate 45 at the back or chosen surface 47 of the wafer. The substrate front surface 49, which is contiguous to the wafer chosen surface 47, is a mirror-like surface for incident light at the selected wavelength $\lambda_0$. If a $\Phi$R or EBR stain or other visually perceptible defect 51 is present on the wafer chosen surface 47, it is likely that a portion of this stain or other visually perceptible defect (difference in color, texture, reflectivity, etc.) will be transferred to the contiguous front surface 49 of the substrate 45. If the wafer 43 is now removed so that the chosen surface 47 of the wafer 43 is no longer contiguous to the substrate front surface 49, as illustrated in FIG. 5, the substrate front surface will be exposed for direct observation. The substrate front surface 49 will contain a visually perceptible (transferred) defect 5 t at a position directly underlying the position where the wafer chosen surface 47 contained a defect 51. Further, the shape of a $\Phi$R or EBR stain or similar visually perceptible defect on the wafer chosen surface 47 will be approximately reproduced as a visually perceptible defect 51t of the same shape and location on the substrate front surface 49. Thus the presence and location of a chemical stain or similar visually perceptible defect on the wafer chosen surface 47 can be determined without direct examination of the wafer chosen surface.

In FIG. 5, an observer's eye or optical sensor array 53 and a source of illumination 55 may be positioned reasonable positions above the exposed substrate front surface 49, to examine this surface for the presence of a visually perceptible defect, such as 51 t. Optionally, a dark surface 57 may be positioned relative to the reflecting surface 49 so that the reflected optical image of the reflecting surface 49 is uniformly dark if and only if no defect 51t is present on the chosen surface.

As an alternative, the substrate front surface 49 may be treated with a selected substance that is highly reflecting for incident light at the selected wavelength $\lambda_0$ and that reacts to the presence of a specified chemical stain or similar defect by changing the color, texture or reflectivity of the surface 49 locally in a visually perceptible manner.

While this invention has been described in terms of several preferred embodiments, modification and variation may be made without departing from the scope of the invention.

We claim:

1. A method for inspecting a surface of a semiconductor wafer for a selected type of defect, the surface of the wafer being initially disposed on a reflecting surface of a support substrate, the method comprising the steps of:
    positioning a reflecting surface contiguous to said semiconductor wafer surface, and allowing a visually perceptible portion of said selected type of defect to appear on said reflecting surface, if said defect is present on said semiconductor wafer surface;
    moving said semiconductor wafer surface and the reflecting surface away from each other so that the reflecting surface is exposed;
    illuminating the reflecting surface with light; and
    examining the reflecting image to determine if said selected type of defect is visually perceptible on any portion of the reflecting surface.

2. The method of claim 1, wherein said examining step further comprises the step of orienting a dark surface relative to said wafer surface and to said reflecting surface so that said reflecting surface appears dark, if no selected type of defect is present on said wafer surface.

3. The method of claim 1, wherein said visually perceptible portion is at least one of a difference in color, texture, and reflectivity compared to other portions of said reflecting surface.

4. The method of claim 1, wherein said visually perceptible portion is of about the same shape as said defect.

5. The method of claim 1, wherein said step of examining the reflected image utilizes an optical sensor array.

6. Apparatus for detecting a selected type of defect on a back surface of a semiconductor wafer, the type of defect being introduced during one or more wafer processing steps, the apparatus comprising:
    a supporting substrate on which the back surface of the semiconductor wafer rests during the wafer processing steps;
    a wafer holder for holding the back surface of said wafer in a position spaced apart from the substrate during a selected time interval, said wafer holder comprising a plurality of movable pins projecting through said substrate to move said back surface into a first position contiguous to said substrate and to translate said back surface away from said substrate to a second position that is spaced apart from said substrate; and
    an imager for forming an optical image of the back surface of said wafer during the selected time interval and for examining the back surface of said wafer for the selected type of defect.

7. The apparatus of claim 6, wherein said supporting substrate includes a reflecting surface that comprises at least a portion of said imager.

8. The apparatus of claim 7 wherein said imager further comprises an optical sensor array.

9. The apparatus of claim 6 wherein said imager comprises an optical sensor array.

10. The apparatus of claim 6 further comprising a light source for illuminating said back surface of said wafer.

11. The apparatus of claim 6 wherein said supporting substrate comprises a chillplate.

12. The apparatus of claim 11 wherein said chillplate comprises a metal coated with Teflon with a cooling liquid circulating in said metal.

13. The apparatus of claim 6, wherein said imager includes a transparent substrate which forms an image of said defect.

14. The apparatus of claim 13 wherein said transparent substrate is provided with a grid.

15. The apparatus of claim 14 wherein said grid is comprised of a first plurality of parallel lines and a second plurality of parallel lines perpendicular to said first plurality of parallel lines.

16. The apparatus of claim 14 wherein said grid comprises a first plurality of concentric circles intersected by a second plurality of radial lines emanating from a center of said concentric circles.

17. Apparatus for detecting a selected type of defect on a surface of a semiconductor wafer, the apparatus comprising:
    a reflecting surface that is initially held against the surface of the semiconductor wafer to allow a visually perceptible portion of a selected type of defect to appear on the reflecting surface, if the defect is present on the surface of the semiconductor wafer;
    a mechanism for moving the reflecting surface and the surface of the semiconductor wafer relative to each other so that the reflecting surface is visible from a selected position above the reflecting surface; and
    a light source for illuminating the reflecting surface so that, if a visually perceptible portion of the selected type of defect is present on the reflecting surface, the presence of this visually perceptible defect is detected by light reflected from the reflecting surface to an observer or an optical sensor array positioned at a selected position.

18. The apparatus of claim 17, further comprising a dark surface, positioned relative to said reflecting surface, so that said reflecting surface appears uniformly dark, if no selected type of defect is present on said reflecting surface.

19. The apparatus of claim 17, where said reflecting surface is treated with a substance that reacts to the presence of a defect by changing at least one of color, texture and reflectivity.

20. The apparatus of claim 17, wherein said visually perceptible portion is at least one of a difference in color, texture, and reflectivity compared to other portions of said reflecting surface.

21. The apparatus of claim 17, wherein said visually perceptible portion is of about the same shape as said selected type of defect.

* * * * *